(12) United States Patent
Hecht et al.

(10) Patent No.: US 7,657,133 B2
(45) Date of Patent: Feb. 2, 2010

(54) SINGLE ANALYTE MOLECULE DETECTION BY FIBRE FLUORESCENCE PROBE

(75) Inventors: Bert Hecht, Riehen/Basel (CH); Philippe Haas, Basel (CH); Andreas Wild, Riehen (CH); Martin Hegner, Riehen (CH); Michel Calame, Riehen (CH)

(73) Assignee: University of Basel (CH)

( * ) Notice: Subject to any disclaimer, the term of this patent is extended or adjusted under 35 U.S.C. 154(b) by 0 days.

(21) Appl. No.: 11/573,800

(22) PCT Filed: Aug. 18, 2005

(86) PCT No.: PCT/IB2005/002444

§ 371 (c)(1),
(2), (4) Date: Jun. 20, 2007

(87) PCT Pub. No.: WO2006/018706

PCT Pub. Date: Feb. 23, 2006

(65) Prior Publication Data

US 2008/0089635 A1    Apr. 17, 2008

Related U.S. Application Data

(60) Provisional application No. 60/602,332, filed on Aug. 18, 2004.

(51) Int. Cl.
*G02B 6/00* (2006.01)
(52) U.S. Cl. ...................................................... 385/12
(58) Field of Classification Search .................... 385/12
See application file for complete search history.

(56) References Cited

U.S. PATENT DOCUMENTS 5,141,312 A    8/1992    Thompson et al.

FOREIGN PATENT DOCUMENTS

| EP | 0383912 A | 8/1990 |
| WO | 2005002444 | 1/2005 |

OTHER PUBLICATIONS

Golden, J.P. et al, "Fluorometer And Tapered Fiber Optic Probes For Sensing In The Evanescent Wave" in Optical Engineering, Soc. of Photo-Optical Instrumentation Engineers. Bellingham, US, vol. 31, No. 7, Jul. 1, 1992, pp. 1458-1462.

(Continued)

*Primary Examiner*—Jerry T Rahll
(74) *Attorney, Agent, or Firm*—Joyce von Natzmer; Pequignot + Myers LLC

(57) ABSTRACT

An apparatus for single analyte molecule detection includes: a light source (20) for generating excitation light; a dichroic mirror (22) disposed on a first path of excitation light generated by the light source, wherein the mirror directs excitation light into a fiber aligner (30); an optical transducer coupled to the light source by the fiber aligner, the optical transducer comprising an optical waveguide (40) made of dielectric material having a first dielectrical index; a photon detector (70) disposed to receive fluorescent back radiation, wherein when a test solution having a second dielectric index lower than the first index is provided and comprises one or more target molecules, excitation light is transmitted by the waveguide and exits a waveguide tip disposed in the test solution so as to excite one or more target molecules; subsequently, the waveguide transmits back radiation along a second path to the photon detector that detects the transmitted back radiation.

18 Claims, 4 Drawing Sheets

OTHER PUBLICATIONS

Thompson, R.B. et al, "Component Selection for Fiber-Optic Fluorometry" in Applied Spectroscopy, The Society For Applied Spectroscopy, Baltimore, US, vol. 44, No. 1, Jan. 1990, pp. 117-122.

Harms, Greg S. et al, "Probing conformational changes of gramicidin ion channels by single-molecule patch-clamp fluoresscence microscopy" in Biophysical Journal, NY, US, vol. 85, No. 3, Sep. 2003, pp. 1826-1838.

US 7,657,133 B2

SINGLE ANALYTE MOLECULE DETECTION BY FIBRE FLUORESCENCE PROBE

This is the U.S. national stage of International application PCT/IB2005/002444, filed Aug. 18, 2005 designating the United States, which claims the benefit of U.S. provisional application 60/602,332, filed Aug. 18, 2004.

FIELD OF THE INVENTION

This invention relates to an apparatus and method for the detection of single analyte molecules in a liquid environment. In particular, the present invention relates to an apparatus and method for qualitatively and quantitatively detecting the concentration of ultralow amounts of analyte molecules in solution using optical waveguide technology.

BACKGROUND OF THE INVENTION

In the art of clinical diagnostics, frequently a diagnostician is faced with the availability of only small sample amounts for testing. Consequently, preparation of samples for testing may result in prepared test solutions having ultralow concentrations of analyte molecules of interest, or the minute amount of available test solution may have an inherent ultralow concentration of analyte to begin with. To address the problem of ultralow concentration of analyte in a test solution, various prior procedures have been developed, such as polymerase chain reaction (PCR) and fluorescence in situ hybridization (FISH). These conventional techniques relying upon amplification technologies are time consuming and expensive to perform. U.S. Pat. No. 5,866,331 to Singer et al. provides an example of single molecule detection by in situ hybridization techniques.

On the other hand, the ability to detect single molecules in a biomedical application without resorting to amplification techniques has certain advantages, and such measurement techniques without amplification have been developed. For example, molecular beacons, such as taught by Tyagi and Kramer, Nature Biotechnology, Vol. 14, March 1996, pp. 303-308, which bind to target molecules and undergo a conformational change upon binding to specific targets are known. Due to the presence of a fluorophore and quencher, the conformational change in the molecular beacon is translated into an optical signal, which can be detected with a high degree of sensitivity. Furthermore, labeled, constrained DNA smart probes make target labeling and consecutive rinsing steps superfluous in methods for detecting DNA and RNA molecules and fragments.

However, the use of fluorescent probes is limited by certain drawbacks as well. Back-ground signals created by the autofluorescence of the optical fiber, the auto-fluorescence of the solution or solvent in which the analyte of interest is dissolved, or the auto-fluorescence and/or Raleigh and Raman scattering generated by the glass components of the optical measuring system itself can create erroneous readings.

This technique also enhances detection of single molecules in a test solution by employing remote sensing, which allows for combined measurements of free-floating molecular switches in low volume cells as well as for micro-fluidic networks. U.S. Pat. No. 5,814,524 by Walt et al. provides an example of an optical sensor apparatus for optical analytical measurements at remote locations.

In addition, it is possible to chemically attach different molecular switches to several sensor fibers and conduct parallel in situ investigation of several different targets of interest, which reduces the time needed to perform diagnostics.

Although setups like this have previously been proposed by Bonnet et al., PNAS, vol. 96, p. 6171, 1999), the principles of signal-collection used by such optical systems are based on the recording of signals that include significant background signals, which severely limits the ultimate detection sensitivity achievable by these methods and apparatuses.

Therefore, there is a need in the art of clinical diagnostics for a sensitive method and apparatus for detecting of low concentrations of analyte molecules that overcomes the drawbacks of the aforementioned methods and apparatuses of the prior art. The present invention endeavors to provide an improved method and apparatus for detecting single analyte molecules in solution that is compatible with, but does not rely upon, conventional amplification techniques, and that is sensitive to the point of being able to detect fluorescence from a single analyte molecule while overcoming the limitations of prior art methods and apparatuses.

Accordingly, a primary object of the present invention is to overcome the disadvantages of the prior art methods and devices for detecting analyte molecules. Another object of the present invention is to provide a method and apparatus for detecting single analyte molecules in solutions that are compatible with amplification techniques, but can be used without them. Another object of the present invention is to provide a method and apparatus for detecting single analyte molecules that is sensitive, easy and convenient to use, and that does not require target labeling and/or consecutive rinsing steps.

Another object of the present invention is to provide a method and apparatus for detecting single analyte molecules that is applicable to miniaturization technologies.

Another object of the present invention is to provide an optical system that performs remote sensing of molecule fluorescence signals and that is especially suited for application to clinical research applications (ex vivo and in vivo), and to practical clinical applications as well.

Another object of the present invention is to provide an optical system that allows in situ measuring of target molecules, thereby making measurements inside the body of a patient possible.

SUMMARY OF THE INVENTION

In accordance with the present objectives, the present invention provides, in a first illustrative apparatus embodiment, an apparatus for single analyte molecule detection that includes: (a) a light source disposed to generate excitation light on a first path; (b) a dichroic mirror disposed on the first path of excitation light generated by the light source, wherein the dichroic mirror is arranged to direct excitation light into a fiber aligner; (c) an optical transducer coupled to the light source by the fiber aligner, wherein the optical transducer comprises an optical waveguide made from a dielectric material having a first dielectric index; (d) a photon detector disposed to receive fluorescent back radiation; and (e) a test solution having a second dielectric index lower than the first dielectric index, wherein the test solution is disposed in a container and comprises one or more target molecules, wherein when a tip of the optical waveguide is disposed in the test solution and excitation light is generated by the light source and transmitted by the optical waveguide so as to exit the tip, one or more target molecules are excited by the excitation light; and wherein, (f) the same optical waveguide is arranged to transmit fluorescent back radiation, generated by one or more excited target molecules, along a second path to the photon detector detecting the transmitted fluorescent back radiation.

In accordance with a second apparatus embodiment of the present invention, the first apparatus embodiment is modified so that the photon detector detects transmitted fluorescent back radiation from a single excited target molecule.

In accordance with a third apparatus embodiment of the present invention, the first apparatus embodiment is modified so that transmitted fluorescent back radiation has a first wavelength and is generated primarily from excited target molecules located in a region of the test solution that is within one half of a first wavelength from the tip of the optical waveguide. In accordance with a fourth apparatus embodiment of the present invention, the third apparatus embodiment is modified so that the optical waveguide provides a portion of both the first path of excitation light and the second path of transmitted fluorescent back radiation. In accordance with a fifth apparatus embodiment of the present invention, the fourth apparatus embodiment is modified so that the dichroic mirror is also disposed on the second path of transmitted fluorescent back radiation.

In accordance with a sixth apparatus embodiment of the present invention, the fifth apparatus embodiment is modified to further include a filter disposed on the second path, wherein the filter filters the fluorescent back radiation. In accordance with a seventh apparatus embodiment of the present invention, the sixth apparatus embodiment is modified to further include a lens disposed on the second path and that focuses the fluorescent back radiation for detection by the photon detector. In accordance with a eighth apparatus embodiment of the present invention, the seventh apparatus embodiment is modified to further include a computer connected to receive signals from the photon detector, wherein the computer provides an interface for reading out a measurement of detected photons of the fluorescent back radiation.

In accordance with a ninth apparatus embodiment of the present invention, the eighth apparatus embodiment is modified so that the photon detector detects transmitted fluorescent back radiation from a single excited target molecule and the computer reads out measurement of detected photons generated by the single excited target molecule. In accordance with a tenth apparatus embodiment of the present invention, the ninth apparatus embodiment is modified so that the tip of the waveguide has a cleaved configuration. In accordance with an eleventh apparatus embodiment of the present invention, the ninth apparatus embodiment is modified so that the tip of the waveguide has a fiber core configured to extend freely over a predetermined length. In accordance with a twelfth apparatus embodiment of the present invention, the ninth apparatus embodiment is modified so that the tip of the waveguide includes a plurality of optic fibers forming a parallel array of an integrated optics device.

The present invention also provides, in a first illustrative method embodiment, a single analyte molecule detection method that includes the steps of: (a) providing an apparatus for single analyte molecule detection comprising: i. a light source for generating excitation light; ii. a dichroic mirror disposed on a first path of excitation light generated by the light source, wherein the dichroic mirror directs excitation light into a fiber aligner; iii. an optical transducer coupled to the light source by the fiber aligner, wherein the optical transducer comprises an optical waveguide made from a dielectric material having a first dielectric index; and iv. a photon detector disposed to receive fluorescent back radiation; (b) providing a test solution having a second dielectric index lower than the first dielectric index and comprising one or more target molecules, wherein a tip of the optical waveguide is disposed in the test solution; (c) generating excitation light using the light source and transmitting the excitation light along a first path into the test solution using the optical waveguide; (d) exciting one or more target molecules in the test solution using the excitation light; (e) generating fluorescent back radiation using the one or more target molecules, then transmitting the back radiation along a second path to the photon detector with the same optical waveguide, wherein the photon detector detects the back radiation.

In accordance with a second method embodiment of the present invention, the first method embodiment is modified to further include the step of: filtering the transmitted back radiation using a filter disposed on the second path. In accordance with a third method embodiment of the present invention, the second method embodiment is modified to further include the step of: focusing the transmitted back radiation using a lens before the back radiation reaches the photon detector. In accordance with a fourth method embodiment of the present invention, the third method embodiment is modified to further include the step of: counting photons of the transmitted fluorescent back radiation detected by the photon detector. In accordance with a fifth method embodiment of the present invention, the fourth method embodiment is modified to further include the step of: sending signals to a computer that provides a read out interface that reads out and displays a measurement of detected and counted photons. In accordance with a sixth method embodiment of the present invention, the first method embodiment is modified so that fluorescent back radiation transmitted by the optical waveguide having a first wavelength comprises substantially of fluorescent back radiation generated by one or more target molecules located in a region of the test solution that is within one half of the first wavelength from the tip of the optical waveguide.

The method and apparatus embodiments, in accordance with the present invention, all serve to provide detection of the presence, and the quantification of the concentration, of ultralow (from nanomolar to attomolar or below) amounts of analyte molecules in solution using an optical waveguide. The present invention takes advantage of the principle wherein the emission of a fluorescent molecule in a dielectric fluid environment (e.g., a test solution) changes according to the distance between the fluorescent molecule in solution and the boundary between the fluid of the test solution and a higher-index dielectric material, such as glass.

As shown in FIG. 1, it is known that the emission pattern of a fluorescent molecule $M_1$ in water, which is a molecule remote from the boundary SB to glass (i.e., a higher-index dielectric) demonstrates no interaction with the higher-index dielectric B. However, fluorescent molecules $M_2$ in water, which are closer to the glass, will interact with the higher order dielectric so as to direct or transmit some of its radiation into the dielectric material. Those fluorescent molecules $M_3$ in a solution, which are close enough to the glass, will transmit the major part of their radiation into the higher-index dielectric body B. The condition where a major part of the fluorescent molecules' radiation is transmitted into the higher-index dielectric body occurs when the distance between the fluorescent molecule and the boundary to the higher-index dielectric is less than half of the excitation wavelength $\lambda$. For example, the distance $d_2$ between the molecule $M_2$ and the boundary between water and glass, as shown in FIG. 1, is less than of the excitation wavelength $\lambda$, so there is some transmission of fluorescent radiation into the dielectric material, glass. However, the distance $d_2$ is not less than $\lambda/2$, so a major part of the emission radiation is not directed into the higher-index dielectric. On the other hand, the molecule $M_3$ is shown as being within one half emission wavelength to the higher-index dielectric material, so a major portion of the emission radiation of molecule $M_3$ is transmitted into the higher-index dielectric. Of course, molecules remote from the higher-index dielectric, such as molecule $M_1$ located at distance $d_1$ (where $d_1 >> \lambda/2$), do not appreciably transmit any of their emission radiation into the dielectric material of higher index.

The method and apparatus embodiments for detecting single analyte molecules, in accordance with the present invention, all operate on the principle that (a) a dielectric body can serve as a waveguide, or as a portion of a waveguide, which can be used to deliver excitation light to target analyte molecules in solution, and (b) only those analyte molecules in solution that are sufficiently close to the surface of the dielectric body, (i.e., the distance of target molecule to surface of dielectric is $<\lambda/2$), will be excited and able to efficiently couple their emitted radiation back into the waveguide. In this manner, the waveguide, constructed to include a high-index dielectric material, can be used to both provide excitation light, and to transmit back emission radiation that is detected by the optical system.

Further objects, features and advantages of the present invention will become apparent from the Detailed Description of Illustrative Embodiments, which follows, when considered together with the attached drawings.

DETAILED DESCRIPTION OF ILLUSTRATIVE EMBODIMENTS

The present invention includes both a method and apparatus for the detection of single analyte molecules in solution. In order to facilitate an easy understanding of the present invention, the apparatus embodiment will be described first.

Figure 2:
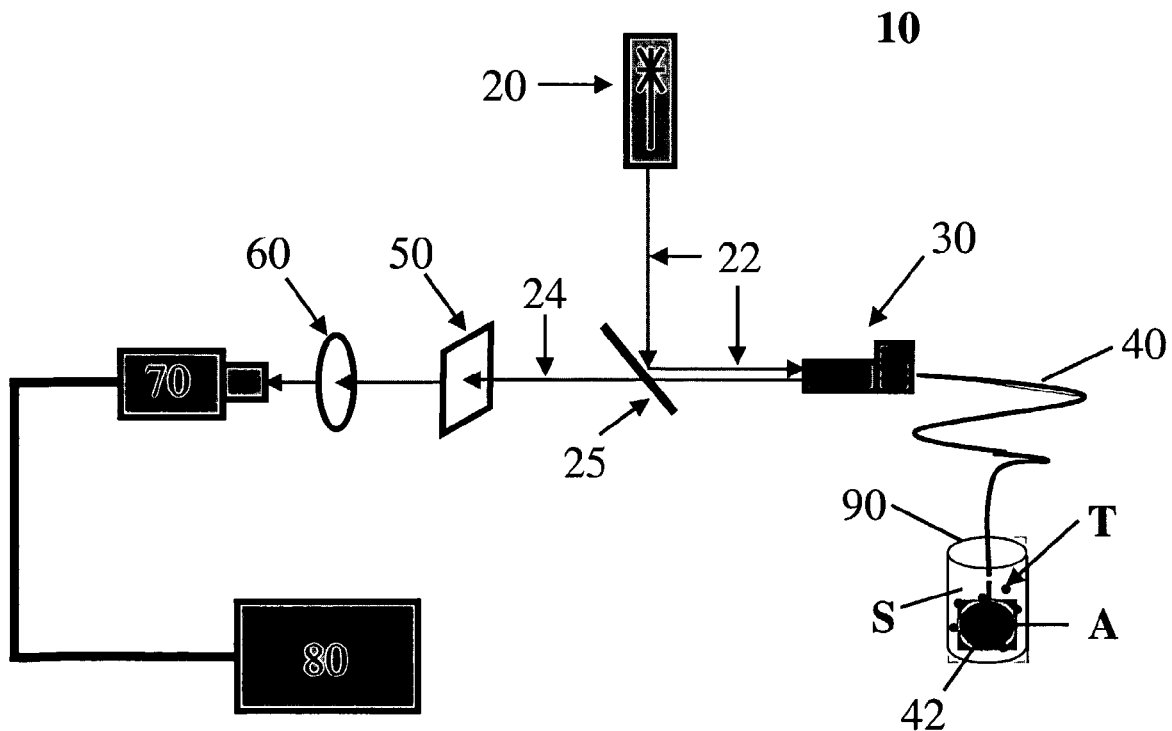
FIG. 2 is a schematic drawing of an illustrative single analyte molecule detection apparatus embodiment in accordance with the present invention.

The apparatus of the present invention is an optical system 10, as shown in FIG. 2, for the remote detection of single analyte target molecules in a solution. This optical system 10 operates on the principle that excitation light 22 delivered by a waveguide 40, made in whole or in part by a dielectric material of higher index than the test solution S, can excite target molecules T of interest thereby causing the target molecules T to emit radiation. In addition, the optical system 10 uses the waveguide 40 to transmit excitation radiation emitted mainly by target molecules that are sufficiently close to the surface of the waveguide (i.e., distance between excited target molecules and the surface of the dielectric waveguide must be less than one half of the wavelength $\lambda$ of the excitation emission radiation).

Optical system 10 includes a light source 20, preferably a laser excitation source, which provides excitation light 22 for exciting fluorescence in certain target molecules T of interest. The wavelength $\lambda$ of the excitation light 22 will depend upon the target molecules T of interest. For example, excitation wavelengths of 633 nm can be provided to excite Cy5-Cy7-FRET (Cyanine Dye 5-Cyanine Dye 7-Fluorescence Resonance Energy Transfer) target molecules. However, those skilled in the art of fluorescent technologies would realize that the present invention is not limited to the use of any particular wavelength of light so long as the light can excite target molecules of interest so as to emit measurable radiation.

Optical system 10 also includes a dichroic mirror 25, a fiber aligner 30, an optical transducer 40, an optical filter 50, a lens 60, a photon detector 70 (i.e., a single photon counting device or APD (Avalanche Photodiode)), and a computer 80. A test solution S containing target molecules T of interest is prepared and presented in a suitable container 90. When in use, the tip of the optical transducer 40 is placed in contact with the solution S.

Specifically, the dichroic mirror 25 is positioned along the path of the excitation light 22 and is used to direct the excitation light 22 into a fiber aligner 30. The fiber aligner 30 couples the light source 20 with an optical transducer 40, which is preferably an optical fiber made of glass, or some other dielectric material, having a dielectric index higher than that of solution S. As known in the art, the optical transducer 40 can be a single optical fiber, or a bundle of optical fibers, surrounded by a protective cover 44. The optical fiber or fibers form the waveguide 42 of the optical transducer 40. The excitation light 22 travels down the optical transducer 40 and exits the tip of the transducer. Optical transducer 40 includes the optical waveguide 42 for the optical system 10. Thus, the optical waveguide is used to transmit excitation light 22 from the light source 20 to target molecules T in the sample solution S. The excitation light 22 that exits from the tip of the optical transducer 40 excites fluorescence of molecules T in solution S by generating an evanescent and or divergent radiation field. Target molecules T in sample solution S are excited by the excitation light 22, and subsequently radiate back radiation 24, which is fluorescent radiation of wavelength $\lambda+\Omega$. Those skilled in the art of fluorescence technologies would realize that the wavelength $\lambda+\Omega$ of the emission radiation depends upon the target molecule T, and that the present invention is not limited to measuring or detecting a particular wavelength or target molecule.

The fluorescence signal generated by the excited molecules is coupled back into the glass of the waveguide 42 so back radiation 24 is transmitted by the optical waveguide 42 and exits the optical transducer 40 as a collimated beam that is transmitted by the dichroic mirror 25. The fluorescent back radiation 24 is then filtered by optical filter 50, and then focused by lens 60 before being sent to be detected by photon detector 70. While the photon detector 70 can be any suitable light detector, it is preferable that the photon detector 70 is a light detector capable of measuring and/or counting one or more single photons. A computer 80, such as a personal computer or the like, is connected to the photon detector 70 so that an interface for reading out the measurement of detected and/or counted photons is provided.

Figure 1:
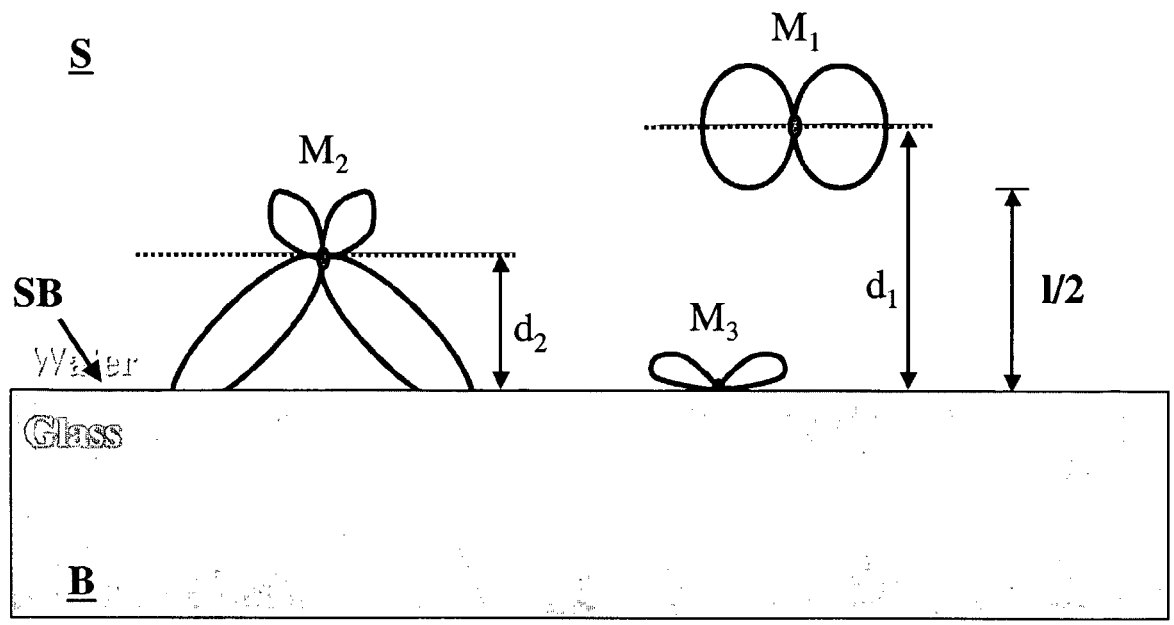
FIG. 1 is a pictorial representation of the change of emission characteristics of a fluorescent molecule in a dielectric medium near a higher index dielectric body (Prior Art).
Figure 5:
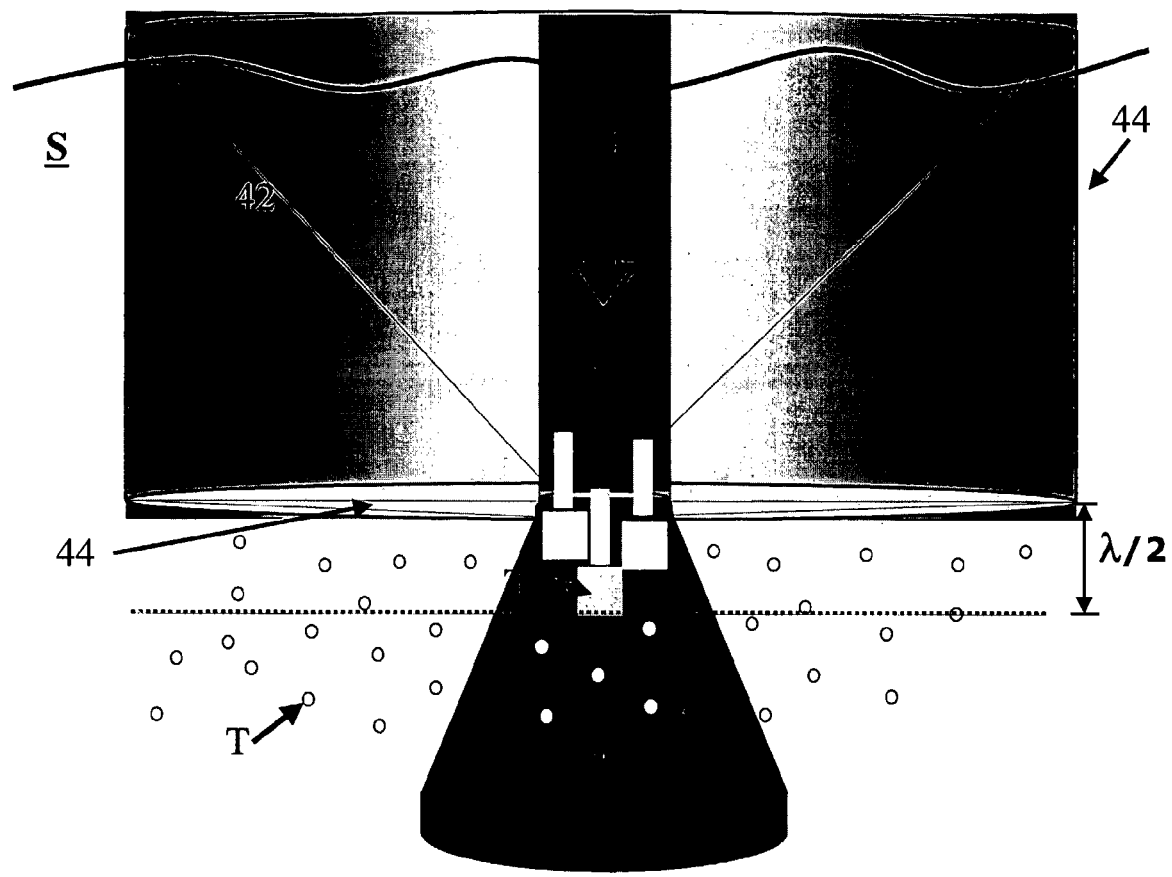
FIG. 5 illustrates the excitation region or detection volume in accordance with the present invention.

As shown in FIG. 1, the emission characteristics of a fluorescent molecule in a dielectric medium (i.e., solution S)

changes when near a higher index dielectric body B. In particular, it is mainly the molecules close to the boundary surface SB that emit the major portion of fluorescence radiation transmitted into the higher index dielectric body B. Due to the nature of the excitation fields provided at the tip 44 of the optical waveguide 42, which are confined to the outside spatial region near the surface of the waveguide, it is mainly molecules within this limited outside region 46 (also referred to as the "excitation region" or the "detection volume") that are preferentially excited by the excitation radiation 22 as shown in FIG. 5. These preferentially excited molecules are also those that will couple back with the waveguide to efficiently transmit fluorescent radiation back up the waveguide. This phenomena of preferential excitation and coupled back transmission of fluorescence within the "excitation region" 46 provides the optical system 10 of the present invention with the ability to detect very low amounts of analyte molecules in solution, even reaching single-molecule sensitivity detection. The excitation region 46 is defined as that portion of the test solution and target molecules that are located within one half of the excitation wavelength from the surface of the tip 44 of the optical waveguide 42, where the wavelength $\lambda+\Omega$. is the wavelength of the fluorescent back radiation emitted by the target molecule(s) T.

Figure 4:
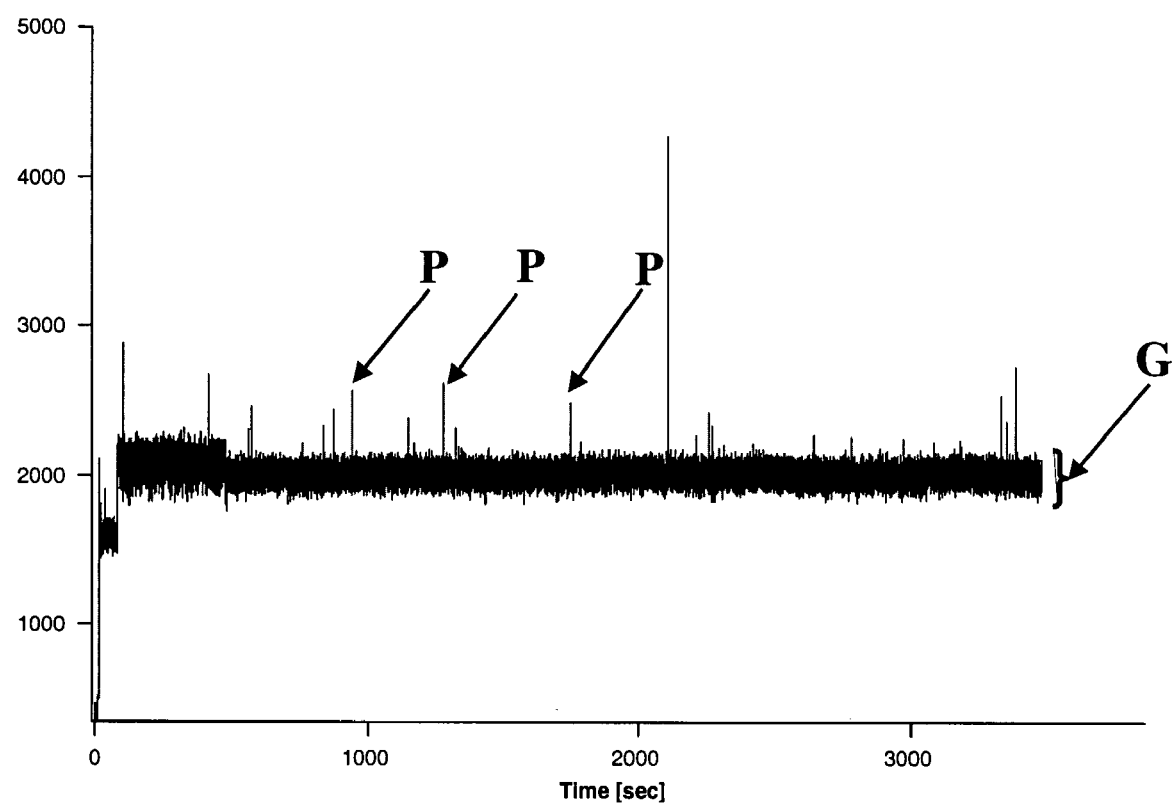
FIG. 4 is a graph representing the trace of fluorescence signal recorded through an optical waveguide of an optical system made in accordance with the present invention (G=Background; P=Fluorescence burst).

This selective transmission feature of the present invention also provides another advantage, which is that while background signals, such as (i) fluorescence generated by chromophores in the far-field of the optical fiber, (ii) auto-fluorescence of the sample solution, and (iii) auto-fluorescence, Rayleigh and Raman scattering generated in the glass of the optical transducer 40 itself, are always generated and cause a continuous background noise, only target molecules T sufficiently close to the glass surface of the optical waveguide contribute to detectable fluorescence bursts. FIG. 4 demonstrates multiple single-molecule fluorescence bursts due to target molecules (i.e., Molecular Beacons) that are readily distinguishable from the background signals in a system 10, constructed in accordance with the present invention. Only those target molecules sufficiently close (i.e., $d<\lambda/2$) to the glass surface of the tip of the waveguide generated these fluorescence bursts. Persons skilled in the art would realize that the optical system 10 of the present invention permits the observance of fluorescence bursts due to single molecules, which can be used to perform fluorescence correlation spectroscopy in a very simple and flexible manner.

Figure 3:
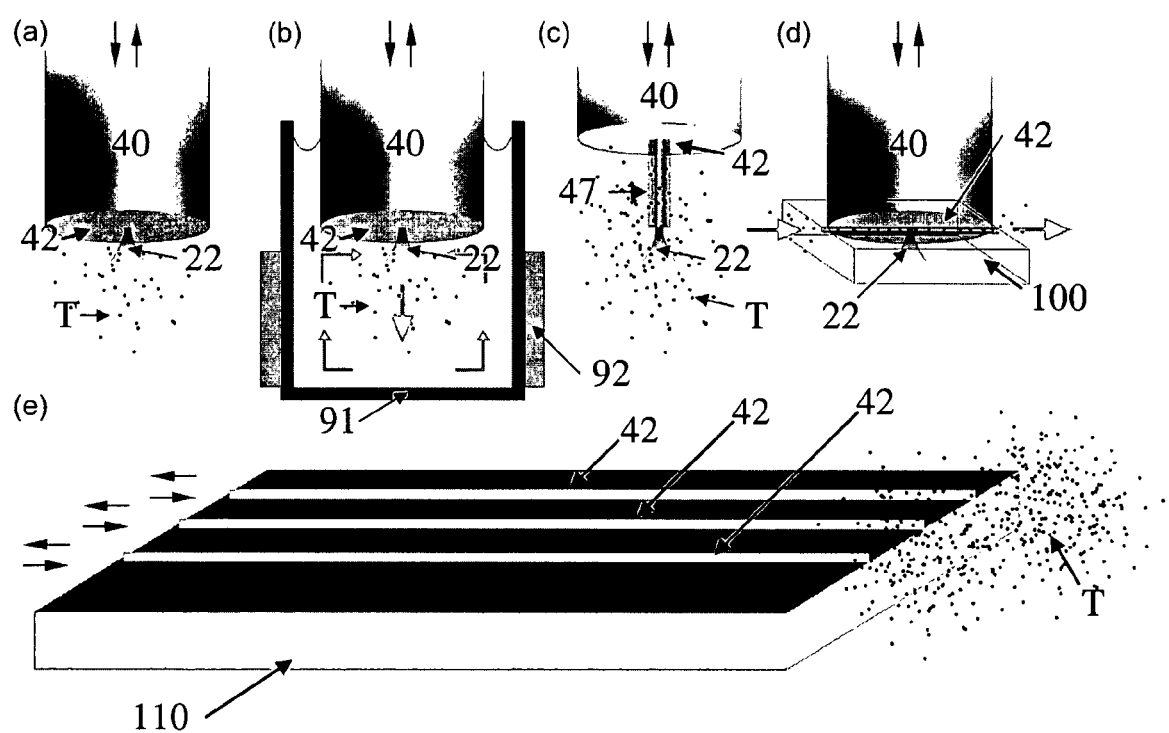
FIG. 3 shows a magnified view of the region A in FIG. 2, which illustrates various illustrative embodiments for the end or tip of the optical transducer and its relationship to a sample volume, including: (a) a cleaved fiber tip placed in an extended sample volume, (b) a cleaved fiber tip placed in a confined sample volume with convection stirring, (c) a fiber core of etched free from the optical fiber, placed in an extended sample volume, (d) a combination of a cleaved fiber tip with a micro-fluidic sample system, and (e) parallelization of cleaved fiber tips using integrated optics for use in an extended sample volume.

FIG. 3 shows five different embodiments for configuring the tip of the optical waveguide 42 in accordance with the present invention. In the tip configuration embodiment shown in FIG. 3(*a*), the waveguide 42 has a cleaved surface through which excitation energy 22 exits to excite target molecules T within the detection volume of the solution S. In the embodiment of FIG. 3(*a*), the detection volume is very small compared to the extended volume of the solution S.

The tip configuration embodiment shown in FIG. 3(*b*) has the same geometry as the waveguide tip shown in FIG. 3(*a*); however, the solution S is a relatively confined sample volume contained in a small container or a microcontainer 91 subjected to convection stirring. Container 91 is provided with heaters 92 for generating the convection current.

The tip configuration embodiment shown in FIG. 3(*c*) includes a fiber core 47 etched free so as to have a predetermined length. The tip configuration shown in FIG. 3(*c*) increases the detection volume while maintaining confined excitation.

The tip configuration embodiment shown in FIG. 3(*d*) combines the tip configuration shown in FIG. 3(*a*) with a microfluidic flow system 100, which provides a microfluidic flow of the test solution through the detection volume located at the cleaved end of the waveguide 42. Lastly, the tip configuration embodiment shown in FIG. 3(*e*) is constructed as an array of optical waveguides 42 of an integrated optical device 110, which is particularly suited for miniaturizing and parallelizing of the system 10.

Having described the apparatus embodiments, in accordance with the present invention, the method embodiment will now be described. The first step of the method of single analyte molecule detection, in accordance with the present invention, involves providing an apparatus for single analyte molecule detection, such as optical system 10, that includes: (a) a light source 20 for generating excitation light 22; (b) a dichroic mirror 25 disposed on a first path of excitation light generated by the light source, wherein the dichroic mirror directs excitation light into a fiber aligner 30; (c) an optical transducer 40 coupled to the light source by the fiber aligner, wherein the optical transducer comprises an optical waveguide 42 made from a dielectric material having a first dielectric index; and (d) a photon detector 70 disposed to receive fluorescent back radiation 24. The first step also includes providing a test solution S having a second dielectric index lower than the first dielectric index and that comprises one or more target molecules T, with a tip of the optical waveguide disposed in the test solution S. The test solution S would be provided in a suitable container 90 or 91.

In the second step of the method, excitation light 22 is generated by the light source 20 and is transmitted by the optical waveguide 42 until it exits the tip of the optical waveguide, such as shown in FIG. 3, which is disposed in the test solution. The excitation light then excites one or more target molecules T in solution S.

In a third step, the one or more excited target molecules subsequently generates fluorescent back radiation 24 that is transmitted by the same optical waveguide 42 along a second path to the photon detector 70. As part of the third step, the transmitted back radiation may be filtered by a filter 50 and focused by a lens 60 before reaching the photon detector 70. In a fourth step, the photon detector 70 detects and/or counts the photons of the transmitted fluorescent back radiation. In a fifth step, the photon detector 70 sends signals to a computer 80, such as a personal computer, which provides a read out interface that reads out and/or displays a measurement of detected and/or counted photons.

In other words, the method of single analyte molecule detection of the present invention includes setting up an optical system, such as the apparatus 10 that includes a light source, one or more optical fibers serving as an optical waveguide, one or more light-coupling devices such as an optical fiber aligner 30, a single photon counting module such as photon detector 70, and a data acquisition board of a computer 80. The setting-up step also includes dipping the cleaved end of the waveguide glass fiber into the test solution S that contains the target molecules T. The light source 20, which generates excitation energy for the fluorophores such as target molecules T, is coupled to the glass fibers of the optical waveguide of the optical transducer.

The optical waveguide 42 serves as both the optical waveguide for the excitation light and for the fluorescence signal (i.e., back radiation) emitted by the excited fluorophores. Excited target molecules emit a fluorescence signal, which is coupled back into the optical fiber or fibers of the waveguide 42 and transmitted and guided to the other end of the waveguide. This transmitted fluorescence signal is then projected onto the photon counting module, such as photon detector 70. The count-rate of photons will vary in accordance with the concentration of target molecules T in solution S, and individual molecules passing near the tip of the optical fiber are detected by corresponding bursts of fluorescence such as shown in FIG. 4. FIG. 4 demonstrates a trace of a fluorescence signal recorded through an optical waveguide of the present invention. Fluorescent energy spikes or bursts, corresponding to single-or several molecules passing within the detection volume at the tip of the waveguide fiber, are shown. The single molecule fluorescence bursts (P) are readily distinguishable from the background (G) fluorescence inherent to the solution S and the optical system 10.

Persons skilled in the art of fluorescent technologies would appreciate that the combination of single-molecule detection/sensitivity and remote sensing technologies using an optical waveguide is new in the field. Single-molecule detection is enabled by nearfield/farfield discrimination, which exploits the specific radiation pattern of molecules close to the interface with higher dielectric constant (i.e., the glass-water interface). Fluorescence is excited via excitation light transmitted by the waveguide, and at the same time, the waveguide collects the emitted fluorescent back radiation from excited analyte molecules using the near-field discrimination technology.

The method and apparatus embodiments in accordance with the present invention were, in particular, designed to operate in combination with constrained nucleic acid probes or molecular switches. Molecular switches, like molecular beacons (See Tyagi and Kramer, Nature Biotechnology, Vol. 14, pp. 303-308, 1996), undergo a conformational change upon binding to specific target molecules. Due to the presence of a fluorophore and quencher, this conformational change is translated into an optical signal, which is detectable with high sensitivity. Furthermore, labeled, constrained DNA probes make target labeling and consecutive rinsing superfluous. A combination of the single analyte molecule detection method of the present invention, which is a near-field optical detection method, with molecular switches directly coupled to the waveguide can be performed to allow a much faster, more specific and more sensitive detection method than current techniques.

The present invention is not limited to combination with any specific constrained nucleic acid probes or specific molecular switches. Any type of constrained nucleic acid probe or molecular switch can be employed, such as molecular switches for detection of peptides and proteins, or any other molecules of interest. This ability of the method and apparatus embodiments, in accordance with the present invention, to be combined with various molecular switches renders the methodology extremely flexible and allows adaptation to other problems.

The above described single analyte molecule detection method is also applicable for use in simultaneous parallel investigation of different pathogens or other molecules by implementing a parallelization as described above (See FIG. 3(e)). The ability to implement the present invention with parallelization, as described above and as shown in FIG. 3(e), is a very important feature of the present invention because it permits the application of the present invention to standard screening techniques to further reduce the time needed to come to conclusive diagnoses.

In addition, the proposed sensor tip configurations demonstrated in FIGS. 3(a) to 3(e) can be miniaturized, which both multiplies the possibilities for the improvement of multi-sensing optical systems and enhances suitability for the use outside of a lab, such as bench-, bed- or even out-side detection applications.

Finally, persons skilled in the art will realize that although current state-of-the-art fluorescent analyte molecule detection technologies are not able to take advantage of the near-field for remote sensing by using the same optical fiber (i.e., the same optical waveguide) for transmitting both excitation light to the target molecules and fluorescent background radiation to the detection sensor, the method and apparatus embodiments in accordance with the present invention all have this feature. Furthermore, the prior art technologies were affected by background noise due to auto-fluorescence, Raleigh and Raman scattering generated by the optical fibers themselves, and the auto-fluorescence from the biological samples that was too intense and compromised the signal to noise ratio thereby limiting detection sensitivity.

Consequently, it was not possible, for all practical purposes, for the prior art technologies to use the very same optical waveguide fiber for both transmitting excitation light energy to the test sample and to collect the fluorescence signal by simultaneously taking advantage of near-field signals emitted by the target molecules. However, the method and apparatus embodiments of the present invention uses appropriate excitation wavelengths and wavelength-shifting fluorescence techniques, as well as the properly constructed optical system 10. In particular, the combination of special glass-properties for the optical transducers (i.e., having a dielectric index higher than that of the test solution), and by using special filters 50, the present invention overcomes the background noise problem that limited the prior art methods and devices.

While the present invention has been described with reference to certain illustrative embodiments, one of ordinary skill in the art will recognize that additions, deletions, substitutions, modifications and improvements can be made while remaining within the spirit and scope of the present invention as defined by the appended claims.

What is claimed is:

1. An apparatus for single analyte molecule detection comprising:
    (a) a light source disposed to generate excitation light on a first path;
    (b) a dichroic mirror disposed on the first path of excitation light generated by the light source, wherein the dichroic mirror is arranged to direct excitation light into a fiber aligner;
    (c) an optical transducer coupled to the light source by the fiber aligner, wherein the optical transducer comprises an optical waveguide made from a dielectric material having a first dielectric index;
    (d) a photon detector disposed to receive fluorescent back radiation; and
    (e) a test solution having a second dielectric index lower than the first dielectric index, wherein the test solution is disposed in a container and comprises one or more target molecules, wherein when a tip of the optical waveguide is disposed in the test solution and excitation light is generated by the light source and transmitted by the optical waveguide so as to exit the tip, one or more target molecules in solution are excited by the excitation light to generate one or more excited target molecules, wherein there is a distance between the excited target molecules and the tip of the optical waveguide and said distance is less than one half of a wavelength $\lambda$ of the excitation light; and wherein,
    (f) the optical waveguide is arranged to transmit fluorescent back radiation, generated by said one or more excited target molecules, along a second path to the photon detector detecting the transmitted fluorescent back radiation of said one or more excited target molecules.

2. An apparatus as recited in claim 1, wherein the photon detector detects transmitted fluorescent back radiation from a single excited target molecule.

3. An apparatus as recited in claim 1, wherein transmitted fluorescent back radiation has a wavelength $\lambda+\Omega$ and is generated primarily from excited target molecules located in a region of the test solution that is within a detection volume defined by said distance.

4. An apparatus as recited in claim 3, wherein the optical waveguide provides a portion of both the first path of excitation light and the second path of transmitted fluorescent back radiation.

5. An apparatus as recited in claim 4, wherein the dichroic mirror is also disposed on the second path of transmitted fluorescent back radiation.

6. An apparatus as recited in claim 5, further comprising a filter disposed on the second path, wherein the filter filters the fluorescent back radiation.

7. An apparatus as recited in claim 6, further comprising a lens disposed on the second path and that focuses the fluorescent back radiation for detection by the photon detector.

8. An apparatus as recited in claim 7, further comprising a computer connected to receive signals from the photon detector, wherein the computer provides an interface for reading out a measurement of detected photons of the fluorescent back radiation.

9. An apparatus as recited in claim 8, wherein the photon detector detects transmitted fluorescent back radiation from a single excited target molecule and the computer reads out measurement of detected photons generated by the single excited target molecule.

10. An apparatus as recited in claim 9, wherein the tip of the waveguide has a cleaved configuration.

11. An apparatus as recited in claim 9, wherein the tip of the waveguide has a fiber core configured to extend freely over a predetermined length.

12. An apparatus as recited in claim 9, wherein the tip of the waveguide includes a plurality of optic fibers forming a parallel array of an integrated optics device.

13. A single analyte molecule detection method comprising the steps of:
  (a) providing an apparatus for single analyte molecule detection comprising:
    i. a light source for generating excitation light;
    ii. a dichroic mirror disposed on a first path of excitation light generated by the light source, wherein the dichroic mirror directs excitation light into a fiber aligner;
    iii. an optical transducer coupled to the light source by the fiber aligner, wherein the optical transducer comprises an optical waveguide made from a dielectric material having a first dielectric index; and
    iv. a photon detector disposed to receive fluorescent back radiation;
  (b) providing a test solution having a second dielectric index lower than the first dielectric index and comprising one or more target molecules, wherein a tip of the optical waveguide is disposed in the test solution;
  (c) generating excitation light using the light source and transmitting the excitation light along a first path into the test solution using the optical waveguide;
  (d) exciting one or more target molecules in solution in the test solution using the excitation light, wherein there is a distance between the excited target molecules and the tip of the optical waveguide and said distance is less than one half of a wavelength $\lambda$ of the excitation light; and
  (e) generating fluorescent back radiation using said one or more target molecules, then transmitting the back radiation along a second path to the photon detector with the optical waveguide, wherein the photon detector detects the back radiation, wherein said method is a single analyte molecule detection method.

14. A method as recited in claim 13, further comprising the step of:
  filtering the transmitted back radiation using a filter disposed on the second path.

15. A method as recited in claim 14, further comprising the step of:
  focusing the transmitted back radiation using a lens before the back radiation reaches the photon detector.

16. A method as recited in claim 15, further comprising the step of:
  counting photons of the transmitted fluorescent back radiation detected by the photon detector.

17. A method as recited in claim 16, further comprising the step of:
  sending signals to a computer that provides a read out interface that reads out and displays a measurement of detected and counted photons.

18. A method as recited in claim 13, wherein fluorescent back radiation transmitted by the optical waveguide has a first wavelength and consists substantially of fluorescent back radiation generated by one or more target molecules located in a a detection volume defined by said distance.

* * * * *